United States Patent [19]

Fang et al.

[11] Patent Number: 5,631,230
[45] Date of Patent: May 20, 1997

[54] RECEPTOR SELECTIVE ANALOGUES OF CHOLECYSTOKININ-8

[75] Inventors: Sunan Fang; Victor Hruby, both of Tucson, Ariz.

[73] Assignee: Arizona Technology Development Corporation, Tucson, Ariz.

[21] Appl. No.: 280,136

[22] Filed: Jul. 25, 1994

Related U.S. Application Data

[63] Continuation of Ser. No. 914,014, Jul. 15, 1992, abandoned, which is a continuation of Ser. No. 410,403, Sep. 21, 1989, abandoned.

[51] Int. Cl.$^6$ ............................ A61K 38/00; C07K 7/00; C07K 7/06
[52] U.S. Cl. ................................. 514/16; 530/328
[58] Field of Search ..................... 530/328; 514/16

[56] References Cited

U.S. PATENT DOCUMENTS 4,400,377  8/1983  Zetler et al. ............................ 514/16

FOREIGN PATENT DOCUMENTS 0226217  6/1987  European Pat. Off. .
0268297  5/1988  European Pat. Off. .

OTHER PUBLICATIONS

Hruby et al, Peptides, 1990, 707–709.
Durieux, et al, vol. 137, Biochemical and Biophysical Research Communication, pp. 1167–1173 (1986).
Sawyer, et al, Abstract, Neural Endocr. Pept. Recept. 5th (1986), pp. 541–552.
Wire et al, Proc. West. Pharmacol. Soc., 33, 65–68, (1990).
Knapp et al, Pharmacology and Experimental Therapeutics, vol. 255, No. 3, 1278–86. 1990.
Wire et al, Proc. West Pharmacol Soc. 34, 453–459 (1991).
Ayres, et al, Proc. West Pharmacol Soc. 34: 477–484, 1991.
Knapp et al, J. of Pharmacology, 191–98, 1991.

*Primary Examiner*—Cecilia J. Tsang
*Assistant Examiner*—S. G. Marshall
*Attorney, Agent, or Firm*—Oblon, Spivak, McClelland, Maier & Neustadt, P.C.

[57] ABSTRACT

Analogues of cholecystokinin-8, which are receptor selective, vary from the normal hormone by alteration of at least one of the two, three or six position amino acids of the natural sequence.

8 Claims, No Drawings

RECEPTOR SELECTIVE ANALOGUES OF CHOLECYSTOKININ-8

This application is a continuation of application Ser. No. 07/914,014, filed Jul. 15, 1992, now abandoned, which is a continuation of Ser. No. 07/410,403, filed on Sep. 21, 1989, now abandoned.

BACKGROUND OF THE INVENTION

1. Field of the Invention

This invention pertains to analogues of cholecystokinin-8 (CCK-8) having high receptor selectivity. Specific amino acid sequence replacements preserve the activity of CCK-8, but allow for receptor selectivity.

2. Background of the Invention

CCK-8, having an amino acid sequence of Asp-Tyr-($SO_3^-$)-Met-Gly-Trp-Met-Asp-Phe-$NH_2$, has been identified as having a wide variety of biological activities. Thus, regulation of pancreatic secretion, gall bladder contraction and gut motility all appear to be at least influenced by CCK-8 release.

Additionally, this hormone is found in high concentrations in the brains of mammals, including humans, and is implicated in a wide variety of neuro-transmitter activities. The list of therapeutic uses for this hormone include control of satiety and gut functions, as well as treatment of a variety of neurological disorders, e.g., treatment of psychotic disfunction. It appears that a plurality of chemo receptors for this compound are found in the brain and the gut.

To realize the therapeutic potential offered by CCK-8, it is necessary to obtain a pharmacologically acceptable compound at least preserving the activity of the natural compound at a particular receptor, but eliminating or drastically reducing activity at other different possible receptors reactive therewith, to control side effects.

SUMMARY OF THE INVENTION

It has now been discovered that site specific alterations of the amino acid sequence of naturally occurring CCK-8 can provide compounds having at least one activity of the natural hormone, but with high receptor selectivity, making it possible to prepare compositions which, in vivo, will effect a single organ system or patient syndrome.

Generically, the amino acid sequence will include

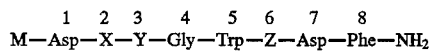

wherein

X=Tyr, Dopa or Tyr($SO_3^-$)

Y=Nle, N-MeNle, Val, D-Val, Phe, D-Phe or Met

Z=Nle or N-MeNle

M=H or $-SO_3^-$

Of course, the critical sequence may be produced as part of a large polypeptide, provided the CCK-8 activity is retained. Smaller sequences, i.e., sequences corresponding to $CCK_{4-8}$ analogues, have also been demonstrated to exhibit activity. In smaller sequences, the presence of the Nle or N-MeNle moieties corresponding to the 6-position amino acid appears to be necessary for selective CCK-8 type activity. Tripeptide analogues also are possible.

DETAILED DESCRIPTION OF THE INVENTION

The novel amino acid sequences of the invention may be made through conventional technologies, and such processes do not constitute an aspect of the invention, per se. Thus, the compounds may be synthesized directly from the amino acid building blocks.

A number of compounds within the generic formula have been prepared. Their preparation is described below. The potency and receptor selectivity of these analogues, along with that of CCK-8, is set forth on the following table.

EXAMPLE I

Preparation of H-Gly-Trp-N-MeNle-Asp-Phe-$NH_2$([N-MeNle$^3$]$CCK_5$)(1)

The title compound was prepared by the solid phase method of synthesis. The p-methylbenzhydrylamine (PMBHA) resin 1.0 g (substitution=1.0 mmol/g) was placed in a 45 ml reaction vessel of a Model 250 Vega automated peptide synthesizer and washed three times with 20 ml of methyl chloride and then allowed to swell overnight in 25 ml methylene chloride. To 0.53 g (2 mmol) of $N^\alpha$-Boc-Phe in approximately 15 ml of methylene chloride (dichloromethane, DCM) was added, 0.31 g (2 mmol) of 1-hydroxybenzotriazole hydrate (HOBt) in 10 ml N,N-dimethylformamide and 0.41 g (2 mmol) of dicyclohexylcarbodiimide (DCC) in 10 ml methylene chloride were then added into the reaction vessel and allowed to react for 30 minutes with continuous shaking. The resin was washed with methylene chloride, absolute ethanol and methylene chloride, 20 ml of each 3 times for 2 minutes, respectively. Approximately 1 mg of resin was then removed and tested with two drops each of a 10% solution of ninhydrin in ethanol, pyridine and phenol (80 g in 20 ml) and heated in an oil bath at 110° C. for 2 minutes to determine if the coupling reaction had gone to completion. The $N^\alpha$-Boc group was removed from the phenylalanine residue with 20 ml of 50% trifluoroacetic acid (TFA) in methylene chloride with 3% anisole, washed and neutralized with 20 ml 10% diisopropylethylamine (DIEA) in methylene chloride 2 times and followed by three times wash with methylene chloride.

In a similar manner, the following protected amino acids were added stepwise to the growing peptide chain: $N^\alpha$-Boc-Asp-β-benzylester; $N^\alpha$-Boc-N-MeNle; $N^\alpha$-Boc-Trp(For); and $N^\alpha$-Boc-Gly. There was obtained, 600 mg $N^\alpha$-Boc-Gly-TrP(For)-N-MeNle-Asp(OBzl)-Phe-Resin.

After the synthesis of the peptide on the resin was completed, the material was removed from the vessel, dried in vacuum, and the peptide was cleaved from the resin support by anhydrous liquid HF (10 ml/g resin) containing 10% anisole and 10% dithioethane at 0° C. for 60 minutes. The excess HF was rapidly removed by vacuum aspiration at room temperature. The mixture was washed with 60 ml of ethyl ether 3 times, and then with 60 ml of ethyl acetate 2 times. The peptide was extracted with 20 ml DMF 2 times and 40 ml glacial acetic acid 3 times. The peptide solution was lyophilized. 600 mg of crude peptide was obtained. The white powder was dissolved in 5 ml of DMF and was applied to a Sephadex G-15 column (3.2×60 cm). Gel fitration (flow 10 ml/hour) yielded several peaks and the major peak was collected and lyophilized to yield a white, fluffy powder 400 mg. A portion of the primary purified peptide obtained (200 mg), was dissolved in 2 ml of DMF and purified on Vydec 218 TP 1010 C18 RP-HPLC column (25 cm×1 cm). Conditions: linear gradient elution starting with 10% acetonitrile ($CH_3CN$) in 0.1% TFA buffer, 1%/min for 30 minutes at a flow rate of 3 ml/min. The more lipophilic impurities were washed from the column with 95% CH$_3$CN in 0.1% TFA buffer for 5 minutes, and after equilibrium (5 minutes 10% CH$_3$CN) the column was ready to use again. After HPLC purification gave the pure peptide 20.0 mg (10% yield) as a white fluffy powder; amino acid analysis: Phe (1.00), Asp (0.90), Gly (1.05), Trp (0.96). N-Methylnorleucine was not determined. The analytical data for the purified product (1) is given in Table 1. Biological activities are found in Table 2.

EXAMPLE II

Preparation of H-Asp-Tyr-N-MeNle-Gly-Trp-N-MeNle-Asp-Phe-NH$_2$ (2)

The title compound was prepared by the solid phase method as outlined above starting with 1.0 g of PMBHA resin and the following protected amino acid were added stepwise to the growing peptide chain: N$^\alpha$-Boc-Phe; N$^\alpha$-Boc-Asp-β-OBzl; N$^\alpha$-Boc-N-MeNle; N$^\alpha$-Boc-Trp(For); N$^\alpha$-Boc-Gly; N$^\alpha$-Boc-N-MeNle; N$^\alpha$-Tyr(Dcb) and N$^\alpha$-Boc-Asp-β-OBzl. To 0.53 g (2 mmol) of N$^\alpha$-Boc-Phe in 20 ml DCM was added 0.31 mg (2 mmol of HOBt in 2 ml DMF and 0.25 g (2 mmol) of 1.3 g diisopropylcarbodiimide (DIC) in 2 ml were then added into the reaction vessel and allowed to react for 30 minutes with continuous shaking, the resin was washed with 20 ml DCM three times each for 2 minutes. Approximately 1 mg of resin was then removed and tested with ninhydrin test. The t-Boc group was removed as described in Example I. In the similar manner, the N$^\alpha$-Boc-Asp-β-OBzl, N$^\alpha$-Boc-N-MeNle were added stepwise to the growing peptide chain. The N$^\alpha$-Boc group was removed from N-methylnorleucine residue with 50% TFA in DCM with 3% anisole for 40 minutes, washed and neutralized with DIEA as described in Example I. The peptide resin obtained H-N-MeNle-Asp-Phe-resin was then removed and tested with the chloranil test to determine if the secondary amino deprotection had gone to completion. To 0.97 g (3 mmol) of N$^\alpha$-Trp(For) in 15 ml DMF was added, 1.33 (3 mmol) of benzotriazol-1-yloxy-tris(dimethylamino)phosphonium hexafluorophosphate (BOP reagent) in 15 ml DMF and 15 ml of 15% DIEA in DMF were then added into the reaction vessel and allowed to react for more than five hours with continuous shaking. The resin was washed with 20 ml of DCM 3 times for 2 minutes. 1 mg of resin was then removed and trested with the chloranil test to determine if the coupling reaction had gone to completion. The N$^\alpha$-Boc group was removed from tryptophan residue with 50% TFA in DCM in 3% anisole, washed and neutralized with DIEA, followed by three washes with DCM. In a similar manner, the following protected amino acids were added stepwise to the growing peptide chain: N$^\alpha$-Boc-N-MeNle; N$^\alpha$-Boc-Tyr (Dcb) and N-Boc-Asp-β-OBzl. There was obtained 1.91 g of N$^\alpha$-Boc-Asp(OBzl)-Tyr(Dcb)-N-MeNle-Gly-Trp(For)-N-MeNle-Asp(Obzl)-Phe-resin. The peptide was cleaved from resin with liquid HF and purified in a manner similar to that employed in Example I. There was obtained 40 mg of the title compound 2 as a white powder. Amino acid analysis: Phe (0.98); Asp (1.98); Gly (1.05); Trp (0.99); Tyr (0.91). N-Methylnorleucine was not determined. The analytical data for the purified product 2 is given in Table 1. Bioligical activities are found in Table 2.

EXAMPLE III

Preparation of H-Asp-Tyr-N-MeNle-Gly-Trp-N-MeNle-Asp-Phe-NH$_2$ Bis-SO$_3^\ominus$(3)

A portion of peptide (2) (20 mg) was treated with pyridine sulfurtrioxide complex (120 mg) in DMF; pyridine (1:1, 2 ml) for 24 hours. The reaction was quenched by the addition of 0.1M ammonium acetate 10 ml, neutralized with 10% aqueous sodium bicarbonate (pH=7.5–8). The sulfated peptide was purified by RP-HPLC column (25×1 cm). Conditions: linear gradient elution starting with 10% acetonitrite in 0.1M NH$_4$OAc solution; 1%/min for 20 minutes at a flow rate of 3 ml/min. After HPLC purification gave the pure peptide 7.5 mg (33% yield) as a white fluffy powder. Amino acid analysis: Phe (0.91), Asp (1.91), Gly (1.05), Trp (0.87), Tyr (1.03); N-methylnorleucine was not determined. The analytical data for the purified product 3 is given in Table 1. Biological activities are found in Table 2.

EXAMPLE IV

Preparation of H-Asp-Tyr-N-MeNle-Gly-Trp-Nle-Asp-Phe-NH$_2$ (4)

The above named compound was prepared as described in Example II, except that N$^\alpha$-Boc-Nle was used in the synthesis instead of N$^\alpha$-Boc-N-MeNle at position 6. There was obtained of 0.92 g of N$^\alpha$-Boc-Asp(OBzl)-Tyr(Dcb)-N-MeNle-Gly-Trp(For)-Nle-Asp(OBzl)-Phe-Resin. The peptide resin was treated with HF as before, the peptide was isolated and then purified as for 2 above. There was obtained 33 mg of the title compound as a white powder. Amino acid analysis: Phe (1.09), Asp (1.98), Gly (1.00), Trp (0.91), Tyr (1.01). N-MeNle was not determined. The analytical data for product 4 is given in Table 1. Biological activities are found in Table 2.

EXAMPLE V

Preparation of H-Asp-Tyr-Nle-Gly-Trp-N-MeNle-AsP-Phe-NH$_2$ (5)

The above named compound was prepared as described in Example II, except that N$^\alpha$-Boc-Nle was used in the synthesis instead of N$^\alpha$-Boc-N-MeNle at position 3. There was obtained 0.90 g of N$^\alpha$-Boc-Asp(OBzl)-TYr(Dcb)-Nle-Gly-Trp(For)-N-MeNle-Asp(OBzl)-Phe-Resin. The peptide resin was treated with HF as before, the peptide was isolated and then purified as for 2 above. There was obtained 29 mg of the title compound 5 as a white powder. Amino acid analysis: Phe (1.06), Asp (2.03), Gly (1.00), Trp (0.89), Tyr (1.08), Nle (0.94). N-MeNle was not determined. The analytical data for product 5 is given in Table 1. Biological activities are found in Table 2.

Example VI

Preparation of H-Asp-Tyr-Val-Gly-Trp-Nle-Asp-Phe-NH$_2$ (6)

The above named compound was prepared as described in Example II, except that N$^\alpha$-Boc-Val and N$^\alpha$-Boc-Nle were used in the synthesis instead of N$^\alpha$-Boc-N-MeNle at positions 3 and 6. There was obtained 0.98 g of N$^\alpha$-Boc-Asp(OBzl)-Tyr(Dcb)-Val-Gly-Trp(For)-Nle-Asp(OBzl)-Phe-Resin. The peptide resin was treated with HF as before, the peptide was isolated and then purified as for 2 above. There was obtained 41 mg of the title compound 4 as a white powder. Amino acid analysis: Phe (0.91), Asp (1.98), Gly (1.05), Trp (0.91), Nle (0.98), Val (0.99), Tyr (0.96). The analytical data for the purified product is given in Table 1. Biological activities are found in Table 2.

EXAMPLE VII

Preparation of H-Asp-Tyr-D-Val-Gly-Trp-Nle-Asp-Phe-NH$_2$ (7)

The above named compound was prepared as described in Example II, except that N$^\alpha$-Boc-D-Val and N$^\alpha$-Boc-Nle were used in the synthesis instead of $N^\alpha$-Boc-N-MeNle at positions 3 and 6. There was obtained 0.99 g of $N^\alpha$-Boc-Asp(OBzl)-Tyr(Dcb)-D-Val-Gly-Trp(For)-Nle-Asp(OBzl)-Phe-Resin. The peptide resin was treated with HF as before, the peptide was isolated and then purified as for 2 above. There was obtained 42 mg of title compound 7 as a white powder. Amino acid analysis: Phe (0.94), Asp (2.01), Gly (1.05), Trp (0.94), Nle (0.96), Val (0.94), Tyr (0.95). The analytical data for the purified product 7 is given in Table 1. The biological activity as found in Table 2.

EXAMPLE VIII

Preparation of H-Asp-Dopa-Nle-Gly-Trp-Nle-Asp-Phe-NH$_2$ (8)

The above named compound was prepared as described in Example II, except that $N^\alpha$-Boc-Dopa was used in the synthesis instead of $N^\alpha$-Boc-Tyr(Dcb) at position 2 and $N^\alpha$-Boc-Nle was used instead of $N^\alpha$-Boc-N-MeNle at positions 3 and 6. There was obtained 0.89 g of $N^\alpha$-Boc-Asp(OBzl)-Dopa-Nle-Gly-Trp(For)-Nle-Asp(OBzl)-Phe-resin. The peptide resin was treated with HF as before, the peptide was isolated and then purified as for 2 above. There was obtained 42 mg of the title compound 8 as a white powder. Amino acid analysis: Phe (0.97), Asp (1.89), Nle (1.91), Gly, (1.00), Trp (0.86), Dopa (1.01). The analytical data for the purified product 8 is given in Table 1. The biological activities are given in Table 2.

EXAMPLE IX

Preparation of H-Asp-Tyr-N-MeNle-Gly-Trp-Nle-Asp-Phe-NH$_2$Bis-SO$_3\theta$(9)

A portion of peptide 4 (20 mg) was treated with pyridine sulfurtrioxide as described in Example III. The peptide was then purified as for 3 above. After HPLC purification gave the pure peptide 7 mg as a white fluffy powder. Amino acid analysis: Phe (0.92), Asp (1.89), Gly (1.00), Trp (0.86), Tyr (0.94), Nle (0.90). N-Methylnorleucine was not determined.

EXAMPLE X

Preparation of H-Asp-Tyr-Nle-Gly-Trp-N-MeNle-Asp-Phe-NH$_2$-Bis-SO$_3\theta$(10)

A portion of peptide (5) (20 mg) was treated with pyridine sulfurtrioxide complex as described in Example III. The peptide was then purified as for 3 above. After HPLC purification gave the pure peptide 6.5 mg as a white fluffy powder. Amino acid analysis: Phe (0.88), Asp (2.02), Gly (1.06), Trp (0.85), Tyr (0.97), Nle (0.93). N-Methylnorleucine was not determined. The analytical data for the purified product 10 is given in Table 1. The biological activities are given in Table 2.

EXAMPLE XI

Preparation of H-Asp-Tyr-Val-Gly-Trp-Nle-Asp-Phe-NH$_2$ Bis-SO$_3\theta$(11)

A portion of peptide 6 (20 mg) was treated with pyridine sulfurtrioxide as described in Example III. The peptide was then purified as for 3 above. After HPLC purification gave the pure peptide 8.1 mg as a white fluffy powder. Amino acid analysis: Phe (0.99), Asp (2.00), Nle (1.01), Gly (1.05), Trp (0.90), Tyr (0.94), Val (0.96). The analytical data for the purified product 11 is given in Table 1. The biological activities are given in Table 2.

EXAMPLE XII

Preparation of H-Asp-Tyr-D-Val-Gly-Trp-Nle-Asp-Phe-NH$_2$Bis-SO$_3\theta$(12)

A portion of peptide 7 (20 mg) was treated with pyridine sulfurtrioxide as described in Example III. The peptide was then purified as for 3 above. After HPLC purification gave the pure peptide 8.1 mg as a white fluffy powder. Amino acid analysis: Phe (1.01), Asp (1.98), Nle (0.95), Gly (1.05), Trp (0.89), Val (0.95), Tyr (0.97). The analytical data for the purified product 12 is given in Table 1. The biological activities are given in Table 2.

TABLE 1

The purity data for CCK analogues

| PEPTIDES | TLC (Rf Value) | | | HPLC | FAB/MS | |
|---|---|---|---|---|---|---|
| | I | II | III | (k' value) | CALC | FOUND |
| H—Asp$^1$—Tyr(SO$_3$)$^2$—Met$^3$—Gly$^4$—Trp$^5$—Met$^6$—Asp$^7$—Phe$^8$—NH$_2$ (CCK-8) | | | | | | |
| 1. [N-MeNle$^6$]CCK$_{4-8}$ | 0.71 | 0.64 | 0.58$^a$ | 4.38 | 649 | 650 |
| 2. [Tyr$^2$ N-MeNle$^3$, N-MeNle$^6$]CCK-8 | 0.78 | 0.66 | 0.67$^a$ | 4.83 | 1054 | 1054 |
| 3. [N-MeNle$^3$, N-MeNle$^6$] CCK-8-Bis-SO$_3^-$ | 0.53 | 0.43 | 0.69$^b$ | 3.29 | 1213 | 1213 |
| 4. [Tyr$^2$, N-MeNle$^3$, Nle$^6$]CCK-8 | 0.68 | 0.65 | 0.65$^a$ | 4.67 | 1040 | 1041 |
| 5. [Tyr$^2$, Nle$^3$, N-MeNle$^6$)CCK-8 | 0.71 | 0.61 | 0.65$^a$ | 4.43 | 1040 | 1042 |
| 6. [Tyr$^2$, Val$^3$, Nle$^6$]CCK-8 | 0.69 | 0.65 | 0.66$^a$ | 4.40 | 1012 | 1012 |
| 7. [Tyr$^2$, D-Val$^3$, Nle$^6$]CCK-8 | 0.69 | 0.65 | 0.66$^a$ | 4.41 | 1012 | 1012 |
| 8. [Dopa$^2$, Nle$^3$, Nle$^6$]CCK-8 | 0.63 | 0.59 | 0.59$^a$ | 3.96 | 1042 | 1042 |
| 9. [N-MeNle$^3$, Nle$^6$]CCK-8-Bis-SO$_3^-$ | 0.49 | 0.34 | 0.65$^b$ | 2.45 | 1199 | 1201 |
| 10. [Nle$^3$, N-MeNle$^6$]CCK-8-Bis-SO$_3^-$ | 0.46 | 0.43 | 0.71$^b$ | 2.68 | 1199 | 1201 |
| 11. [Val$^3$, Nle$^6$]CCK-8-Bis-SO$_3^-$ | 0.43 | 0.61 | 0.65$^b$ | 3.25 | 1172 | 1172 |
| 12. [D-Val$^3$, Nle$^6$]CCK-8-Bis-SO$_3^-$ | 0.43 | 0.41 | 0.65$^b$ | 3.26 | 1172 | 1172 |

TLC solvent system as follows:
[a]I. n-butanol/acetic acid/water/pyridine 15:3:10:12 II. n-butanol/acetic acid/pyridine/water 6:1.2:6:4.8 III. ethyl acetate/pyridine/acetic acid/water 60:20:6:1.
[b]I. isobutanol/formic acid/water/pyridine 75:16:9:20 II. isobutanol/formic acid/pyridine/water 17:2.5:10:2.5 III. isopropanol/formic acid/pyridine/water 18:4:6:2.

The analytical data for the purified product 9 is given in Table 1. The biological activities are given in Table 2.

TABLE 2

Inhibition of [¹²⁵I] CCK-8 Binding by CCK-8 Analogues

| Compound | Guinea Pig Brain IC$_{50}$ (nM) | Guinea Pig Pancreas IV$_{50}$ (nM) | Rat Brain IC$_{50}$ (nM) | Rat Pancreas IC$_{50}$ (nM) | Ratio Pancreas/Brain Rat (Guinea Pig) | |
|---|---|---|---|---|---|---|
| H—Asp¹—Tyr(SO₃—)²—Met³—Gly⁴—Trp⁵—Met⁶—Asp⁷—Phe⁸—NH₂ (CCK-8) | | | 0.322 | 0.129 | 0.40 | — |
| 1 [N-MeNle⁶]CCK$_{4-8}$ | 3.34 | 8,004 | 4.67 | >10,000. | >2,000. | (2396) |
| 2 [Tyr², N-MeNle³, N-MeNle⁶] CCK-8 | 0.23 | 958 | 0.131 | 1030. | 7,863. | (4146) |
| 3 [N-MeNle³, N-MeNle⁶] CCK-8-Bis-SO₃— | | | 1.41 | 0.46 | 0.29 | — |
| 4 [Tyr², N-MeNle³, Nle⁶] CCK-8 | | | 1.45 | 46.7 | 32.2 | — |
| 5 [Tyr², Nle³, N-MeNle⁶] CCK-8 | | | 976. | 170.2 | 0.17 | — |
| 6 [Tyr², Val³, Nle⁶] CCK-8 | | | 0.318 | 10.64 | 33.5 | — |
| 7 [Tyr², DVal³, Nle⁶] CCK-8 | | | 1.26 | 521. | 413. | — |
| 8 [Dopa², Nle³, Nle⁶] CCK-8 | | | 9.70 | 0.975 | 0.0010 | — |
| 9 [N-MeNle³, Nle⁶] CCK-8-Bis-SO₃— | 3.19 | 29,073 | — | — | — | (9099) |
| 10 [Nle³, N-MeNle⁶] CCK-8-Bis-SO₃— | | | 0.496 | 1.392 | 2.81 | — |
| 11 [Val³, Nle⁶] CCK-8-Bis-SO₃— | | | 0.318 | 10.64 | 33.46 | — |
| 12 [DVal³, Nle⁶] CCK-8-Bis-SO₃— | | | 9.11 | 360. | 39.5 | — |

Pharmacological compositions will be prepared in a fashion similar to those incorporating CCK-8. Thus, the analogue is combined with a pharmacologically acceptable carrier, which carrier will vary, depending on the mode of administration which may include oral/parenteral, IM, IV, etc. Method of administration, and carrier, will also depend on the activity and analogue selected. The preparation of a wide variety of administerable forms, including compounding the analogues of the invention with carriers, excipients, adjuvants, etc., will be familiar to those of ordinary skill in the art. Dosage ranges will vary on the basis of the analogue selected and the activity desired, but will again be similar to those employed for CCK-8. In general, a dosage range of 1 ug/kg to 1 mg/kg may be employed.

The above invention has been described by reference to a generic formula, as well as specific embodiments. Variations of those embodiments, and additions thereto, within the general description, will occur to those of ordinary skill in the art without the exercise of inventive facility. Unless indicated otherwise, exemplification of the invention is not intended to be limiting, save for the express limitations presented in the claims appended hereto.

What is claimed as new and desired to be secured by letters patent of the United States is:

1. A receptor selective analogue of cholecystokinin-8, having the amino acid sequence

```
  1    2   3  4   5    6   7    8
M—Asp—X—Y—Gly—Trp—Z—Asp—Phe—NH₂
``` wherein

X is Tyr or Dopa

Y is N-MeNle, Val, D-Val, Phe or D-Phe

Z is Nle or N-MeNle, and

M is H or —SO₃⁻, and exhibiting a pancreatic receptor/brain receptor selectivity ratio, measured by ¹²⁵I-cholecystokinin-8 binding inhibition, of less than 0.40 or in excess of 30.

2. A pharmaceutical composition, comprising the analogue of claim 1, and a pharmacologically acceptable carrier.

3. A receptor selective analogue of cholecystokinin-8, having a biological activity of cholecystokinin-8 and exhibiting a pancreatic receptor/brain receptor selectivity ratio, measured by ¹²⁵I-cholecystokinin-8 binding inhibition, of less than 0.40 or in excess of 30, having residues of the peptide

```
  4   5   6   7    8
Gly—Trp—Z—Asp—Phe—NH₂
``` wherein Z=N-MeNle.

4. The analog of claim 1, wherein said amino acid sequence is (Tyr², N-MeNle³, N-MeNle⁶) CCK-8.

5. A receptor selective analogue of cholecystokinin-8, having the amino acid sequence

```
  1    2   3  4   5    6   7    8
M—Asp—X—Y—Gly—Trp—Z—Asp—Phe—NH₂
``` wherein

X is Tyr or Dopa

Y is Nle, N-MeNle, Val, D-Val, Phe or D-Phe

Z is N-MeNle, and

M is H or —SO₃⁻, and exhibiting a pancreatic receptor/brain receptor selectivity ratio, measured by ¹²⁵I-cholecystokinin-8 binding inhibition, of less than 0.40 or in excess of 30.

6. A pharmaceutical composition comprising the analog of claim 5, and a pharmacologically acceptable carrier.

7. A receptor selective analogue of cholecystokinin-8, having the amino acid sequence

```
  1    2   3  4   5    6   7    8
M—Asp—X—Y—Gly—Trp—Z—Asp—Phe—NH₂
``` wherein

X is Dopa

Y is Nle, N-MeNle, Val, D-Val, Phe or D-Phe

Z is Nle or N-MeNle, and

M is H or —SO₃⁻, and exhibiting a pancreatic receptor/brain receptor selectivity ratio, measured by ¹²⁵I-cholecystokinin-8 binding inhibition, of less than 0.40 or in excess of 30.

8. The analog of claim 7, wherein Y and Z are both Nle.

* * * * *